United States Patent [19]
Shi

[11] Patent Number: 5,470,589
[45] Date of Patent: Nov. 28, 1995

[54] HARDENING AGENT FOR AFFECTED TISSUES OF THE DIGESTIVE SYSTEM

[75] Inventor: Zhao-Qi Shi, Peking, China

[73] Assignee: Traditional Chinese Medicine Research Laboratory, Inc., Matsuyama, Japan

[21] Appl. No.: 86,853

[22] Filed: Jul. 7, 1993

Related U.S. Application Data

[63] Continuation of Ser. No. 690,762, Apr. 24, 1991, Pat. No. 5,252,344.

[30] Foreign Application Priority Data

Apr. 25, 1990 [JP] Japan ................................ 2109787
Apr. 19, 1991 [JP] Japan ................................ 3115319

[51] Int. Cl.⁶ .................. A61K 33/06; A61K 31/70; A61K 47/12; A61K 35/78
[52] U.S. Cl. ................ 424/698; 514/25; 514/783; 424/195.1
[58] Field of Search .............. 514/25, 783; 424/698, 424/195.1

[56] References Cited

U.S. PATENT DOCUMENTS 4,094,969  6/1978  Batzer et al. ................. 424/78.01
4,395,398  7/1983  Yamamoto ..................... 424/145

FOREIGN PATENT DOCUMENTS 0146714  9/1982  Japan .
9216810  12/1984  Japan .
1016982  1/1986  Japan .
1226812  9/1989  Japan .

OTHER PUBLICATIONS

Tulleken, J. E. et al., New Eng. J. Med. 321:55, Jul. 6, 1989 (Abstract).
Endres, S. et al., New Eng. J. Med. 320:265–271, Feb. 2, 1989 (Abstract).
Laudanno, O. N. et al., Ital. J. Gastroenterol. 22(1):19–21, Feb. 1990 (Abstract).
Crampton, J. R. et al., Scand. J. Gastroenterol. Suppl. 125:113–118, 1986 (Abstract).

*Primary Examiner*—Raymond Henley, III
*Assistant Examiner*—William R. A. Jarvis
*Attorney, Agent, or Firm*—Foley & Lardner

[57] ABSTRACT

The hardening agent contains a composition comprised of tannic acid and potassium aluminium sulfate in a ratio of tannic acid to potassium aluminium sulfate ranging from 10 to 1 to 1 to 50 and a stabilizing agent extracted from crude drugs of plants containing a phenol, flavon, flavonoid, catechin or a polycarboxylic acid.

4 Claims, No Drawings

HARDENING AGENT FOR AFFECTED TISSUES OF THE DIGESTIVE SYSTEM

This application is a continuation of Ser. No. 07/690,762 filed Apr. 24, 1991, now U.S. Pat. No. 5,252,344.

BACKGROUND OF THE INVENTION

1. Field of the Invention

The present invention relates to a hardening agent for hardening affected tissues of the digestive system and, more particularly, to a hardening agent for hardening the affected tissues of the digestive system, suitable for curing the affected tissues thereof by withering, hardening, fixing or fibrillating the affected tissues thereof by injecting a medicine or agent in a non-operative way into the esophagophleboma, piles, the site of the rectal prolapse, the site of the prolapse of the rectal mucosa and the affected uplift tissues (carcinomatous polyps) of the large intestine and the rectum under observation by the proctoscope or endoscope or under X-ray examination.

2. Description of Related Art

Conventional hardening agents for curing the esophagophleboma and the piles of a light or intermediate degree include, for example, ethanol amine of oleic acid, polydecanol, phenol almond oil and so on. The tumor of the digestive system is subjected to percutaneous ethanol injection therapy.

The piles of a severe degree, the rectal prolapse and the prolapse of the rectal mucosa are treated in an operative way.

Heretofore, as the method for non-operatively curing the esophagophleboma and the piles, there has been employed hardening therapy for hardening the affected tissues by injecting various hardening agents into the affected tissues. Focuses of the affected tissues are brought into an inactive state by withering, hardening, fixing or fibrillating the focuses thereof due to the embolism of the blood vessels of the affected tissues or due to the inflammation-induced repair reaction of the peripheral tissues. This hardening therapy requires neither general anesthesia nor laparotomy. Hence, the risk is so small that this therapy presents the advantage that it can extensively be applied to weakening patients or old patients. Desirable conditions for a hardening agent include strong astringency and hemostatic effect. The aseptic inflammation reaction induced by injection of the hardening agent can reduce the extent of edema, congestion and exudation if the acute inflammation reaction could be eliminated for a short period of time, thereby capable of preventing the affected tissues from causing necrosis. When the aseptic inflammation reaction has been transferred to its chronic inflammation phase, then the tissues are withered, hardened, fixed and fibrillated and the focuses disappear. Hence, the desired curing object can be achieved.

The conventional hardening agents, however, are limited in uses, as will be described hereinafter. More specifically, such hardening agents as having strong action require injection under direct examination by X-rays while admixing a contrast medium with the hardening agent, because there is the risk of necrosing the tissues if they would be leaked from the blood vessels. On the other hand, hardening agents having mild action is so applied as to harden the affected tissues by withering, hardening, fixation or fibrosis by injecting the tissues of the focal site outside the blood vessels with the hardening agents. Hence, in a state that the veins are varicose, the hardening agents are little employed solely. Particularly, for large esophagophleboma, a two-step therapy is employed such that the hardening agent having stronger action is injected directly into the vessels, while the hardening agent having milder action is injected into the surrounding tissues. Thus, the kinds of the hardening agents should be chosen in accordance with the condition of a disease, and multi-injection required is laborious. Particularly, in curing the piles, the hardening agents are so adapted as to be effective for a small amount of bleeding and a light degree of the prolapse of the anus, however, they are not so adapted as to be effective for such cases as requiring digital replacement of the anal prolapse caused during defecation or as being slipping down from the anus and being ordinarily out of place. These cases require operative curing. Further, operative reparative fixation is applied to cases of the rectal prolapse and the prolapse of the rectal mucosa, however, they are out of adaptation of the hardening agents.

SUMMARY OF THE INVENTION

Therefore, the present invention has the object to provide a hardening agent for hardening the affected tissues of the digestive organs so adapted as to be effectively applicable to the rectal prolapse, the prolapse of the rectal mucosa; the piles of a severe degree, and the affected uplift tissues (carcinomatous polyps) of the large intestine and the rectum which could not so far be treated and cured by the conventional agents, while solving the disadvantages and problems inherent in the conventional hardening agents and ensuring effectiveness and safety.

In other words, the present invention relates to an aqueous hardening agent comprising a plurality of ingredients having action for the embolism of the blood vessels or action for hardening the tissues. The hardening agent preferably has the pharmacological properties as follows: (1) the aseptic acute inflammation reaction to be caused by injection of the hardening agent is so light with respect to the extent of edema and congestion and so short with respect to the period of time of inflammation due to the presence of an agent having action of astringency; (2) its action of causing the embolism of the blood vessels is accurate and appropriate and the tissues cause no necrosis even if injected outside the vessels; and (3) the fibrosis of the tissues can be completed without leaving any stiffness in the course of repairing the chronic inflammation. The action of the tissues for repairing the inflammation can wither and inactivate the focuses. By the fixation of the tissues, the digestive organ is returned to its original position, without causing any risk of slipping down. The hardening agent according to the present invention is an aqueous injectable preparation so that it does not cause any side effect, such as the embolism of the vessels of the remote organs as reported for oleaginous, injectable preparations.

The present invention has another object to provide a hardening agent for hardening the affected tissues of the digestive system, which is stable for a long period of time under room temperature and under conditions with light shaded.

In order to achieve the aforesaid objects, the present invention consists of a hardening agent for hardening affected tissues of the digestive system, which comprises a composition containing tannic acid and potassium aluminum sulfate in a ratio of tannic acid to potassium aluminium sulfate ranging from 10 to 1 to 1 to 50 and containing a stabilizer comprising an extract from crude drags originating from plants.

As a result of review on classical literature on Chinese traditional medicine, it is found that, back 2,000 years ago, publication titled "Emperor's Canon of Internal Medicine" describes to the extent that "piles are the result of blood vessels dilatation which may occur through abnormal defecation" and it has already implied that there is a relationship of occurrence of the piles with extension of the vessels and abnormal defecation. Literature entitled "Plain Questions" sets forth the principle of a non-surgical therapy of "elevating the fallen" for the prolapse of the piles and the anal prolapse. Historical medical books introduce various methods and preparations on the basis of the theory of traditional Chinese medicine stating that "sour drugs may be used as astringent and punchery substance to control prolapse". The books include, for example, "Compendium of Materia Medica", "Dan Xi Xin Fa" and "Tu Shu Ji Cheng". For instance, the book entitled "Dan Xi Xin Fa" states that "gallnut, alum, . . . treat piles to fumigate and to wash by decoction".

It is to noted that the main ingredient of gallnut is tannic acid which has strong action of astringency against the tissues as well as action of contracting the blood vessels and suppressing a variety of microorganisms. It further has anti-exudation. And aluminium ion in a solution of potassium aluminium sulfate as an ingredient of white alum causes inflammation on the local tissues and hardens and fibrillates them.

The hardening agent according to the present invention has the action of hardening, fixing and fibrillating the site of the esophageal wall, the rectal wall and the anal canal into which the agent has been injected, thereby hardening and curing the affected tissues of the digestive organs.

The hardening agent according to the present invention contains an additive comprising an extract originating from crude drugs of plants such as, for example, *Zingberis rhizoma, Mori folium*, gallnut (*Schinsandrae fructus*), *Plantaginis semen, Magnolicae cortex, Carthami flos, Aurantii pericarpium*, rosemary (*Rosmarinus officinalis* L.), sage (*Salvia officinalis* L.), thyme (*Thymus vulgaris* L.), marjoram (*Origanus majorana* Moerch), oregano (*Origanum vulgare* L.), clove (*Eugenia caryopyllata* Thumb), ginger (*Zingiber officinale* Roscoe), nutmeg (*Myristica fragrans* Houtt), mace (*Myristica fragrans* Houtt), turmeric (*Curcuma longa* L.), cinnamon (*Cinnamomunzeylanicum blue*), pepper (*piper nigrum* L.), and so on. The extract may preferably contain a phenol, flavon, flavonoid, catechin or polycarboxylic acid. The additive can stabilize the composition containing tannic acid and potassium aluminium sulfate, and the ratio of tannic acid to potassium aluminium sulfate ranges preferably from 10 to 1 to 1 to 50. The hardening agent according to the present invention in the form of an injectable preparation can be stored for a long period of time in a stable way.

Description will then be made of test procedures and results. The tests includes acute toxicity test, inflammation-induced test on hind paws of rats, cotton pellets granuloma test for rats, vessel endothelial cell injury test, esophageal walls tissue injury-induced fibrillation test for dogs, anorectal canal tissue injury-induced fibrillation test for rabbits, antibacterial test, carcinogenic tests for enteric administration of carcinogens to rats, the kind of preparations and stability test for preparations.

Acute Toxicity Test

The injectatable preparations of the hardening agents according to the present invention were intravenously or intraperitoneally administered to groups of rats, each group consisting of 10 male mice of αα-type having weight of 20 grams plus or minus 2 grams. The results of death were observed in seven days after administration and the lethal dose 50 ($LD_{50}$, ml/kg) was computed according to the Richfield-Wilcockson method. The test results are shown in Table 1 below.

TABLE 1

| Present Invention | Lethal Dose 50 ($LD_{50}$, ml/kg) | |
|---|---|---|
| | i.v. | i.p. |
| Preparation (1) | 8.2 plus or minus 0.4 | 22.5 plus or minus 0.9 |
| Preparation (2) | 7.6 plus or minus 0.3 | 19.8 plus or minus 0.7 |

Inflammation-Induced Test on Hind Paws of Rats

1. Test Procedures

The hardening agents of the present invention, commercially available hardening agent and physiological saline were administered to groups of rats, each group consisting of 13 female and male rats having weight of 220 grams plus or minus 20 grams and a variation in the volume of the hind paw (edema or swelling) was periodically measured. The rat's hind paw on one side was administered with the hardening agent in the amount of 0.15 ml and with physiological saline in the amount of 0.15 ml as a control. The volumes of the hind paws were measured in 1 hours, 3 hours, 5 hours, 12 hours, 24 hours, 72 hours, and 120 hours after administration and the acute inflammation reaction was considered using an average increase value or rate of the hind paws causing inflammation as an indicator.

2. Test Results

The inflammation reaction was recognized in each group into which the hardening agent was administered. The extent of inflammation and days of duration of inflammation were in the descending order of 5% phenol almond oil, preparation (2) and preparation (1). The control into which physical saline was administered was light in the extent of inflammation and the inflammation induced in this control group was recovered within short. The test results are shown in Table 2 below.

TABLE 2

| | Inflammation-Induced Test on Hind Paws of Rats | | | | | | | |
|---|---|---|---|---|---|---|---|---|
| | Average Volume of Hind Paws before Inflammation (ml) | Average Rate of Increasing Hind Paws after Injection (ml) (edema rate, %) | | | | | | |
| | | 1 hour | 3 hour | 5 hour | 12 hour | 24 hour | 72 hour | 120 hour |
| Preparation (1) | 0.97 | 0.96** 98.9% | 1.08** 111.3% | 1.22** 125.7% | 0.92** 94.8% | 0.79** 81.4% | 0.25* 25.7% | 0.11 11.3% |

TABLE 2-continued

| | Average Volume of Hind Paws before Inflammation (ml) | Average Rate of Increasing Hind Paws after Injection (ml) (edema rate, %) | | | | | | |
|---|---|---|---|---|---|---|---|---|
| | | 1 hour | 3 hour | 5 hour | 12 hour | 24 hour | 72 hour | 120 hour |
| Preparation (2) | 1.01 | 1.10** 108.9% | 1.22** 120.7% | 1.35** 133.6% | 1.19** 117.8% | 0.96** 95.0% | 0.51* 50.4% | 0.30* 29.7% |
| 5% phenol almond oil | 0.98 | 1.15** 117.3% | 1.33** 135.7% | 1.48** 151.0% | 1.41** 143.8% | 1.30** 132.6% | 0.95** 96.9% | 0.78** 79.6% |
| Physiological saline | 1.00 | 0.145 14.5% | 0.162 16.2% | 0.26 26% | 0.18 18% | 0.06 6% | — | — |

Notes:
*P < 0.01
**P < 0.001

Cotton Pellets Granuloma Tests for Rats

1. Test Procedures

The cotton pellets impregnated with the hardening agents of the present invention, commercially available hardening agent or physiological saline were subcutatneously embedded on the back of the rat to thereby form granuloma. The granuloma induced by the cotton pellet was removed in seven days after administration and the weight of the granuloma was measured. The tests were carried out by etherizing the rats and embedding aseptic cotton pellets (weighing 20 mg plus or minus 1 mg) impregnated with 0.1 ml of the hardening agent according to the present invention, 0.1 ml of the commercially available hardening agent or 0.1 ml of physiological saline under the dermis on the back of the rat. In seven days after embedding, the rats were killed to bleed by cutting their heads and the granuloma induced by the cotton pellets was removed and weighed by electronic balance.

2. Test Results

The weight of the cotton pellets granuloma was in the descending order of the preparation (1), the preparation (2), 5% phenol almond oil and physiological saline. The test results are shown in Table 3 below.

TABLE 3

Cotton Pellets Granuloma Tests for Rats

| Test Agents | No. of Rats | Weight of Cotton Pellets Granuloma | t-Acceptance |
|---|---|---|---|
| Preparation (1) | 10 | 485 mg plus or minus 55.12 mg | P < 0.001 |
| Preparation (2) | 10 | 430 mg plus or minus 43.38 mg | P < 0.001 |
| 5% Phenol almond oil | 10 | 297 mg plus or minus 50.23 mg | P < 0.01 |
| Physiological saline | 10 | 176 mg plus or minus 12.28 mg | — |

Vessel Endothelial Cell Injury Tests

1. Procedures for Preparation of Samples

The vessel endothelial cells were obtained by treating the umbilical veins of the newborn with trypsin in conventional manner and subcultured in RITC80-7 culture medium. The resulting cell suspension was employed for tests. The materials to be tested includes the preparation (1) of the hardening agent of the present invention, the preaparation (2) thereof, and a 5% ethanol amine oleate (EO) solution. The test materials were employed as 2-fold, 5-fold, 10-fold, 20-fold and 100-fold dilution.

2. Test Procedures

A mixture of 50 microliters of the hardening agent of the aforesaid concentration with 50 microliters of the aforesaid cell suspension was mixed with 100 microliters of a 0.2% trypan blue dyeing solution. Immediately after mixing, the resulting mixture was transferred to a hemacytometer and the number of pigment-dyed dead cells was computed, thereby calculating a viability rate of cells. A control group in which only the culture medium was added to the vessel endothelial cell suspension gave a viability rate of cells as high as 80%.

The extent of injury of cells induced by addition of the hardening agent was rated from severe (+++), intermediate (++), low (+), and very low (−). The severe rating (+++) of injury means that the viability rate of the cells ranges from 0% to 20%; the intermediate rating (++) of injury means the viability rate of the cells ranging from 20% to 50%; the low rating (+) of injury means the viability rate of the cells ranging from 50% to 80%; and the very low rating (−) of injury means the viability rate of the cells ranging from 80% or higher. As diluting solutions were employed physiological saline and serum.

3. Results

The hardening agents diluted to a low extent caused injury in the vessel endothelial cells. It is further noted that a lower concentration of the hardening agent changes the extent of injury from severe rating to low rating. The results may vary with the kind of the hardening agent. It can be noted, however, that dilution with serum has reduced the action caused by injury. Further, the extent of injury of the vessel endothelial cells corresponds to an initial stage of the vessel embolism action of the affected tissues. The test results are shown in Table 4 below.

TABLE 4

Injury of Vessel Endothelial Cells of Rats by Hardening Agents

| Hardening Agent | Diluting Solution | Dilutions of Hardening Agents | | | | |
|---|---|---|---|---|---|---|
| | | 2-fold | 5-fold | 10-fold | 20-fold | 100-fold |
| Preparation (1) | Physiological saline | +++ | +++ | +++ | − | − |
| Preparation (1) | Serum | +++ | ++ | + | − | − |
| Preparation | Physiolo- | +++ | +++ | +++ | − | − |

TABLE 4-continued

Injury of Vessel Endothelial Cells of Rats by Hardening Agents

| Hardening Agent | Diluting Solution | Dilutions of Hardening Agents | | | | |
|---|---|---|---|---|---|---|
| | | 2-fold | 5-fold | 10-fold | 20-fold | 100-fold |
| tion (2) Preparation (2) | cal saline Serum | +++ | ++ | + | − | − |
| 5% EO | Physiological saline | +++ | +++ | +++ | + | − |
| 5% EO | Serum | +++ | +++ | +++ | − | − |

Esophageal Wall Tissues Injury-Induced Fibrillation Tests for Dogs

1. Method of Operation

Fifteen mixed-breed dogs having weight ranging from 8 kg to 12 kg were grouped into three groups. The dogs went on a fast for a day before operation and intravenously administered dropwise with 500 ml of a Ringer's mixture with 1 gram of cefamezine, and they were intravenously anaesthetized with pentobarbital sodium at the rate of 20 mg per kilogram of the body weight. After anaesthesia, the pleura mediastinum was cut open to expose and incise the lower esophagus lengthwise and administered with the preparation (1) and the preparation (2) of the hardening agent according to the present invention and a 5% phenol almond oil (briefly called Pao hereinafter) solution in the quantity of 1 ml through a 27G two-step injectable needle under direct examination. After the bleeding has stopped completely, the pleura mediastinum cut open was seamed with silky thread while inserting a drain. After the air was removed, the drain was removed.

2. Test Procedures

After injection of the testing hardening agents into three groups of dogs, the dogs were killed periodically, i.e. day 1, 3, 7, 14 and 28, and the esophagus was taken out. The esophagus taken out was visually observed for states of the mucosa and serofluid of the site into which the agent has been injected, in terms of edema, necrosis and ulceration, and the results are rated from severe (+++), intermediate (++), light (+) and low (−).

After visual observation, the esophagus taken out was sliced in a width as small as 3 mm and fixed by a 10% formalin solution. Thereafter, the sliced tissues were further sliced to a thickness of 3 microns by a microtome and then dyed with hematoxylin-eosine for microscopic observation for cytoinfiltration, fibrocyte, fibrosis and an extent of curing injury or damages of tissues of the newborn vessels.

3. Test Results

Acute inflammation such as edema and cytoinfiltration was observed in each of the groups in which the agent was administered. The extent and days of duration in this case were in the descending order of the 5% phenol almond oil solution, the preparation (2) and the preparation (1). The extent of chronic inflammation reaction such as fibrocyte and fibrosis was in the descending order of the preparation (1), the preparation (2) and the 5% phenol almond oil solution. The results are shown in Table 5 below.

TABLE 5

| Day after Operation | Hardening Agents | Visual and Histological Observations | | | | | | |
|---|---|---|---|---|---|---|---|---|
| | | Necrosis | Edema | Cytoinfiltration | Ulceration | Newborn Vessels | Fibroblast | Fibrillation |
| Day 1 | Prep. (1) | − | ++ | ++ | − | − | − | − |
| | Prep. (2) | − | ++ | ++ | − | − | − | − |
| | Pao | ++ | +++ | ++ | − | − | − | − |
| Day 3 | Prep. (1) | − | − | + | − | − | + | − |
| | Prep. (2) | − | + | + | − | − | + | − |
| | Pao | ++ | +++ | +++ | ++ | − | − | − |
| Day 7 | Prep. (1) | − | − | − | − | ++ | +++ | ++ |
| | Prep. (2) | − | − | − | − | ++ | +++ | ++ |
| | Pao | + | − | + | + | + | + | − |
| Day 14 | Prep. (1) | − | − | − | − | +++ | +++ | +++ |
| | Prep. (2) | − | − | − | − | +++ | +++ | +++ |
| | Pao | − | − | − | − | ++ | ++ | ++ |
| Day 28 | Prep. (1) | − | − | − | − | +++ | +++ | +++ |
| | Prep. (2) | − | − | − | − | +++ | +++ | +++ |
| | Pao | − | − | − | − | +++ | +++ | +++ |

Anorecral Canal Tissue Injury-Induced Fibrillation Tests

1. Method of Operation

Fifteen domestic rabbits of white type having weight from 2.8 kg to 3.2 kg were equally grouped into three groups. The rabbits went on a fast for a day before operation and an enema of 10 ml of glycerin solution was applied on the day of operation. The rabbits were intravenously administered dropwise with 100 ml of a 5% glucose solution containing 0.5 gram of cefamezine, and they were anaesthetized by intravenous administration of pentobarbital sodium at the rate of 25 mg per kilogram of the body weight. After anaesthesia, the peritoneum was cut open by celiotomy to expose and incise the rectum and anal canal lengthwise and the preparation (1) or the preparation (2) of the hardening agent of the present invention or a 5% phenol almond oil solution (briefly called Pao hereinafter) was injected in the quantity of 0.3 ml through an order-made 29G two-step injectable needle under direct examination. After the bleeding has been stopped, the lengthwise incised rectal and anal canal portions were sutured with silky thread while inserting a drain and closing the stomach. The drain was removed after discharging the solution from stomach.

2. Test Procedures

After injection of the testing hardening agents into three groups of the rabbits, the rabbits were killed periodically, i.e. day 1, 3, 5, 7 and 14, and the rectal and anal canal were taken out. The organ sections taken out was visually observed for states of the mucosa and serofluid of the site into which the agent has been injected, in terms of edema, necrosis and ulceration, and the results are rated from severe (+++), intermediate (++), light (+) and low (-).

After visual observation, the organ sections taken out were sliced in a width as small as 3 mm and fixed by a 10% formalin solution. Thereafter the sliced tissues were sliced to a thickness of 3 microns by a microtome and then dyed with hematoxylin-eosine for microscopic observation for cytoinfiltration, fibrocyte, fibrosis and an extent of curing injury or damages of tissues of the newborn vessels.

3. Test Results

Acute inflammation such as edema and cytoinfiltration was observed in each of the groups in which the agent was administered. The extent and days of duration in this case were in the descending order of the 5% phenol almond oil solution, the preparation (2) and the preparation (1). The extent of chronic inflammation reaction such as fibrocyte and fibrosis was in the descending order of the preparation (1), the preparation (2) and the 5% phenol almond oil solution. The results are shown in Table 6 below.

TABLE 7

Antibacterial Tests

| Method of Tests | Dilutions of Preparation (1) | E. coli | B. subtilis | Staph. aureus | Ps. aeruginosa | Clostridium sp. |
|---|---|---|---|---|---|---|
| Plate | stock soln | - | - | - | - | - |
| Plate | 1:3 | - | - | - | - | - |
| Plate | 1:10 | - | - | - | - | - |
| Plate | 1:30 | + | - | - | - | - |
| Test Tube | stock soln | - | - | - | - | - |
| Test Tube | 1:3 | - | - | - | - | - |
| Test Tube | 1:10 | - | - | - | - | - |
| Test Tube | 1:30 | + | - | + | + | + |

Carcinogenic Tests by Enteric Administration of Carcinogen

TABLE 6

| Day after Operation | Hardening Agents | Necrosis | Edema | Cytoinfiltration | Ulceration | Newborn Vessels | Fibroblast | Fibrillation |
|---|---|---|---|---|---|---|---|---|
| Day 1 | Prep. (1) | - | ++ | ++ | - | - | - | - |
| | Prep. (2) | - | ++ | ++ | - | - | - | - |
| | Pao | ++ | +++ | ++ | ++ | - | - | - |
| Day 3 | Prep. (1) | - | - | + | - | - | ++ | - |
| | Prep. (2) | + | + | + | - | - | ++ | - |
| | Pao | ++ | ++ | +++ | ++ | - | - | - |
| Day 5 | Prep. (1) | - | - | - | - | ++ | +++ | +++ |
| | Prep. (2) | - | - | - | - | ++ | ++ | +++ |
| | Pao | + | - | + | + | + | + | - |
| Day 7 | Prep. (1) | - | - | - | - | +++ | +++ | +++ |
| | Prep. (2) | - | - | - | - | +++ | +++ | +++ |
| | Pao | + | - | - | - | + | + | + |
| Day 14 | Prep. (1) | - | - | - | - | +++ | ++ | +++ |
| | Prep. (2) | - | - | - | - | +++ | ++ | +++ |
| | Pao | - | - | - | - | +++ | +++ | ++ |

Antibacterial Tests

The preparation (1) of the hardening agent according to the present invention was tested for its antibacterial activity by plate method and test tube method in conventional manner. The solid culture media employed for plate method were prepared by adding a mixture of given amounts of L-cystein, agar, sodium chloride, glucose, yeast extract and casein peptone with 50 ml of the preparation (1) to 920 ml of water, dissolving them in a warm bath and pouring a given amount of the culture medium in dishes which in turn were sterilized in an autoclave at 121° C. for 20 hours and employed for tests followed by the return to room temperature. On the other hand, the liquid culture media to be employed for the test tube method were prepared by using the same mixture, except for agar, and pouring the media into test tubes with cotton lids. The test tubes were employed in the same manner after sterilization in conventional manner. The incubation was carried out in both cases in an incubator at 37° C. for 3 days.

The antibacterial activity of the preparation (1) was determined as active when a colony or colonies was or were visually observed on the incubated plate culture media, while as inactive when no colory was visually observed thereon. On the other hand, for the test tube method, the preparation (1) was determined as active when the culture medium was transparent, while as inactive when the culture medium was turbid. In Table 7, the minus sign means active and the plus sign means inactive.

to Rats

The enteric administration of carcinogens to rats may cause tumors on the distocolon and the rectum. It is to be noted herein that the group of rats in which feed containing a large amount of animal fats and oil has been fed for a long period of time particularly after administration of the carcinogens may cause tumors at a higher probability than the group in which feed containing a standard amount of animal fats has been fed. It has been found that the administration of the hardening agents according to the present invention to the affected tissues of the rats under endoscopic observation can suspend propagation of the affected uplift tissues. Thus, this method of curing can prolong the life of the rats. Test procedures and test results will be described hereinafter.

1. Test Procedures

Fifty male rats of F344 type weighing from 120 grams plus or minus 20 grams were grouped into four groups, two out of the four groups, each consisting of twenty male rats and two ouf of the four groups, consisting of five rats. The rats of the two groups, each consisting of twenty rats, and of the one out of the two groups, each consisting of five rats, were administered with a carcinogen as N-methyl-N'-nitro-N-nitrosoguanidine (MNNG) by injecting a 0.25% aqueous solution of MNNG to the depth of 3 cm from the anus using a polyethylene tube at the rate of 0.3 ml per once a day consecutively for four hours after anaesthesia to a light degree with ether prior to enteric administration. A control group of rats consisting of five rats was likewise administered with physiological saline. The standard-fat feed contained swine fats at the rate of 20%, while the high-fat feed contained fats at the rate of 5%. The rats in the three groups were fed with the standard-fat feed during a period of time for which MNNG has been administered, and the group consisting of twenty rats treated with the hardening agent of the present invention as preparation (5) was fed with the high-fat feed after the four week duration of administration with MNNG, while the non-treated group consisting of twenty rats was fed with the high-fat feed and the non-treated group consisting of five rats was further fed with the standard-fat feed. The control group of five rats which had been treated with physiological saline was fed continuously with the standard-fat feed over the entire period of test time. The rats with the preparation (5) of the present invention administered were periodically examined for distocolon and rectum by an endoscope. When the affected uplift tissues of the digestive organ of the rats were recognized, then the preparation (5) of the hardening agent of the present invention was locally injected in the amount of 0.05 ml to 0.5 ml into the affected tissues thereof and the tissues surrounding the affected tissues. The duration for feeding the rats lasted 18 months after administration of the MNNG or the physiological saline, and all the rats alive after the duration of feeding were killed to observe the presence or absence of tumors on the distocolon and the rectum.

2. Test results

It can be noted that the number of the alive rats of the rats in the three groups to which MNNG had been administered was decreasing as the duration of feeding elapses. For the two groups in which the rats were fed with the high-fat feed, cases such as malappetite, reduction in body weight, bloody excrement, etc. were recognized and the rats have caused the anal prolapse, obstruction of the intestines and intussusception. It can be noted that, for the non-treated groups, the number of the alive rats has decreased to a statistically significant extent, as compared with the groups treated with the preparation (5) of the present invention. The number of the alive rats in the three groups was found to be twenty-one rats after of a lapse of eighteen months of feeding and it was found that the number of tumors per one rat ranged from five to twelve and that an average per one rat was 8.2 tumors. It can further be noted that the rats in the groups treated with the preparation (5) of the present invention has caused fibrillation of the affected tissues and granulation, however, no newborn tumors were recognized. The test results are shown in Table 8 below.

Description will be made of the preparations for the hardening agents according to the present invention.

PREPARATION (1)

| Tannic acid from *Schinsandrae fructus* | 0.15 gram |
| --- | --- |
| Potassium aluminium sulfate | 4.00 grams |
| Sodium citrate | 1.50 grams |
| Dextran 40 | 1.00 gram |
| Glycerin | 10.00 grams |
| Extract from crude drugs of various plants* or** | 4.00 ml |
| Sodium hydrogen sulfite | 0.10 gram |
| Disodium calcium edetoate | 0.01 gram |
| Distilled water (adjusted to pH 4–5 with a pharmacologically intoxic acid or alkali) | to make 100 ml |

Notes:
*The various plants contain *Zingberis rhizoma, Mori folium, Schinsandrae fructus, Plantaginis semen, Magnolicae cortex, Carthami flos* and *Aurantii pericarpium* and they were extracted with 2 ml of an ethanol aqueous solution.
**The various plants include rosemary, sage, thyme, marjoram, oregano, clove, ginger, nutmeg, mace, turmeric, cinnamon and pepper, and the plants were extracted with 2 ml of an ethanol aqueous solution and ampouled in the amount of 10 ml into colorless hard-glass amboules and sterilized under high-pressurized steam in conventional way. The gases contained in the ampoules were replenished with nitrogen gas.

PREPARATION (2)

| Tannic acid from *Schinsandrae fructus* | 0.20 gram |
| --- | --- |
| Potassium aluminium sulfate | 2.00 grams |
| Sodium citrate | 1.50 grams |
| Dextran 40 | 1.00 gram |
| Glycerin | 10.00 ml |
| Sodium hydrogen sulfite | 0.10 gram |
| Disodium calcium edetoate | 0.01 gram |
| Distilled water (adjusted to pH 4–5 with a pharmacologically intoxic acid or alkali) | to make 100 ml |

The solution in the amount of 10 ml was poured into colorless glass ampoules which in turn were sterilized with

TABLE 8

Carcinogenic Tests by Enteric Administration of Carcinogen to Rats

| Duration of Administration of MNNG or Physiological Saline (4 weeks; Standard-Fat Feed) | Kind of Feed after Administration of MNNG or Physiological Saline | Months of Feeding after Administration of MNNG or Physiological Saline & (No. of Alive Mice) | | | | t-Acceptance |
| --- | --- | --- | --- | --- | --- | --- |
| | | 0 | 6 | 12 | 18 | |
| Group of Administration of MNNG | | | | | | |
| Non-Treated Group | Standard | (5) | (5) | (4) | (3) | — |
| Group of Prep. (5) | High-Fat | (20) | (19) | (17) | (15) | <0.01 |
| Non-Treated Group | High-Fat | (20) | (18) | (10) | (3) | <0.01 |
| Control Group of Administration of Physiological Saline | Standard | (5) | (5) | (4) | (4) | — | high-pressurized steam in conventional manner and which were replenished with nitrogen gas.

PREPARATION (3)

This preparation (3) was employed by dissolving the preparations A and B on place.

Preparation A

| Tannic acid from *Schinsandrae fructus* | 0.015 gram |
| --- | --- |
| Extract from crude drugs of various plants* | 0.20 ml |
| Sodium hydrogen sulfite | 0.01 gram |
| Distilled water | 10.00 ml |
| (adjusted to pH 4–5 with a pharmacologically intoxic acid or alkali) | |

Notes:
*The various plants contain *Zingberis rhizoma, Mori folium, Schinsandrae fructus, Plantaginis semen, Magnolicae cortex, Carthami flos* and *Aurantii pericarpium* and the crude drugs were extracted with an ethanol aqueous solution.

A solution of the preparation A was filtered by suction using a 0.22-micron membrane filter and the filtrate was poured into ampoules or vials which in turn were cooled and frozen well to allow ice to sublime under high vacuum condition and the resulting preparation to dry.

Preparation B

| Potassium aluminium sulfate | 4.00 grams |
| --- | --- |
| Sodium citrate | 1.50 grams |
| Dextran 40 | 1.00 gram |
| Glycerin | 10.00 ml |
| Disodium calcium edetoate | 0.01 gram |
| (adjusted to pH 4–5 with a pharmacologically intoxic acid or alkali) | |

The colorless hard glass ampoules were poured at the rate of 10 ml and sterilized under high-pressurized steam.

PREPARATION (4)

The preparation (4) was prepared by dissolving it on site.

| Tannic acid from *Schinsandraw fructus* | 0.20 gram |
| --- | --- |
| Potassium aluminium sulfate | 4.00 grams |
| Sodium citrate | 1.00 grams |
| Dextran 40 | 1.00 gram |
| Extract from crude drugs of various plants* | 4.00 ml |
| Sodium hydrogen sulfite | 0.05 gram |
| Disodium calcium edetoate | 0.01 gram |
| Distilled water | to make 100 ml |
| (adjusted to pH 4–5 with a pharmacologically intoxic acid or alkali) | |

Notes:
*The various plants contain *Zingberis rhizoma, Mori folium, Schinsandrae fructus, Plantaginis semen, Magnolicae cortex, Carthami flos* and *Aurantii pericarpium* and extracted with an ethanol aqueous solution.

A solution of the preparation (4) was filtered by suction using a 0.22-micron membrane filter and the filtrate was poured in the amount of 10 ml into ampoules or vials which in turn were cooled and frozen well to allow ice to sublime under high vacuum condition and the preparation to dry.

PREPARATION (5)

| Tannic acid | 4.00 grams |
| --- | --- |
| Potassium aluminium sulfate | 4.00 grams |
| Sodium citrate | 0.30 gram |
| Dextran 40 | 2.00 gram |
| Conc. glycerin | 2.50 ml |
| Chlorobutanol | 0.30 gram |
| Extract from crude drugs of various plants | 2.00 grams |
| Sodium hydrogen sulfite | 0.10 gram |
| Sodium edetoate | 0.01 gram |
| Distilled water | to make 100 ml |
| (adjusted to pH 4–5 with a pharmacologically intoxic acid or alkali) | |

Notes:
*The various plants contain orange skin, orange and lemon were extracted with 4 ml of an ethanol aqueous solution.

The preparation was poured into 50-ml colorless glass vials and sterilized with under high pressures in conventional manner. The vials were replenished with nitrogen gas.
Stability Tests for Preparations Colorless hard glass ampoules were filled with 10 ml of a composition of the hardening agents according to the present invention. After the ampoules were replenished with nitrogen gas, they were sterilized at 121° C. for 20 minutes by steam under high pressures in conventional manner. The hardening agents according to the present invention were aquous after sterilization and the colors are colorless or pale yellow.

Under various storage conditions, the preparations (1) and (2) are tested for stability for a long period of time. The preparation (1) was stable for three years and three months under conditions under which light scattered in a room. The preparation (1) turned yellow in a relatively short period of time under exposure to light (Xenon lamp) under room temperature. On the other hand, the preparation (2) was found stable for six months under light scattering conditions in a room and turned yellow in a short period of time under conditions under which Xenon lamp has been exposed at room temperature. The test results are shown in Tables 9 and 10.

TABLE 9

Tests for Stabilizing Preparations under Light Scattering Conditions in Room

| Storage conditions: | Light scattering conditions in room at room temperature (white light, 100 lux) | |
| --- | --- | --- |
| Storage vessel: | Colorless hard glass ampoules (five ampoules in a paper box) | |
| Preparations: | Preparation (1) and preparation (2) | |
| Storage Duration (months) | Preparation (1) | Preparation (2) |
| 0 | Colorless-pale yellow | Colorless-pale yellow |
| 1 | Colorless-pale yellow | Colorless-pale yellow |
| 2 | Colorless-pale yellow | Colorless-pale yellow |
| 3 | Colorless-pale yellow | Colorless-pale yellow |
| 6 | Colorless-pale yellow | Colorless-pale yellow |

TABLE 9-continued

Tests for Stabilizing Preparations
under Light Scattering Conditions in Room

| | | |
|---|---|---|
| 12 | Colorless-pale yellow | yellow |
| 18 | Colorless-pale yellow | yellow |
| 24 | Colorless-pale yellow | yellow |
| 30 | Colorless-pale yellow | yellow-brown |
| 36 | Colorless-pale yellow | yellow-brown |
| 39 | Colorless-pale yellow | yellow-brown |

TABLE 10

Tests for Stabilizing Preparations
under Light Exposing Conditions in Room

| Storage conditions: | Light exposing conditions in room at room temperature (Xenon light) | |
|---|---|---|
| Storage vessel: | Colorless hard glass ampoules | |
| Preparations: | Preparation (1) and preparation (2) | |
| Storage Duration (months) | Preparation (1) | Preparation (2) |
| 0 | Colorless-pale yellow | Colorless-pale yellow |
| 1 | Colorless-pale yellow | Colorless-pale yellow |
| 2 | Colorless-pale yellow | Colorless-pale yellow |
| 3 | Colorless-pale yellow | yellow yellow |
| 10 | Colorless-pale yellow | Colorless-pale yellow |
| 14 | yellow | yellow-brown |

TABLE 10-continued

Tests for Stabilizing Preparations
under Light Exposing Conditions in Room

| | | |
|---|---|---|
| 24 | yellow | yellow-brown |

The hardening agents according to the present invention show hardening activity of the affected tissues of the digestive system. Further, the present invention can provide the novel hardening agents for curing the esophagophleboma, piles and affected uplift tissues (carcinomatous polyps).

The hardening agents according to the present invention can demonstrate stability for a long period of time under shaded conditions and secure excellent quality.

What is claimed is:

1. An injectable preparation for hardening the tissue of digestive organs comprising a tissue-hardening effective amount of tannic acid and potassium aluminium sulfate as well as a stabilizing agent extracted from crude drugs of plants selected from the group consisting of *Zingberis rhizoma, Mori folium*, Schinsandrae cortex, Carthami sage, thyme, marjoram, oregano, clove, ginger, nutmeg, mace, turmeric, cinnamon, pepper and combinations thereof.

2. The injectable preparation as claimed in claim 1, wherein the stabilizing agent is an extract of aromatic crude drugs of the plants containing essential oil or an extract from the crude drugs of the plants containing organic acids.

3. The injectable preparation as claimed in claim 1, wherein the stabilizing agent contains phenol, flavon, flavonoid, a catechin or a polycarboxylic acid.

4. The injectable preparation as claimed in claim 1, wherein the ratio of tannic acid to potassium aluminium sulfate ranges from 10 to 1 to 1 to 50.

* * * * *